United States Patent [19]
Lee

[11] 3,941,120
[45] Mar. 2, 1976

[54] VENTILATING ENDOSCOPES

[76] Inventor: Shaotsu Thomas Lee, 121 Waialeale St., Honolulu, Hawaii 96825

[22] Filed: Jan. 16, 1975

[21] Appl. No.: 541,403

Related U.S. Application Data

[63] Continuation of Ser. No. 249,665, May 2, 1972, abandoned.

[52] U.S. Cl. ........................... 128/4; 128/8
[51] Int. Cl.² ........................... A61B 1/00
[58] Field of Search ............ 128/4–11, 145.8, 128/351; 37/61

[56] References Cited
UNITED STATES PATENTS

| | | | |
|---|---|---|---|
| 3,319,627 | 5/1967 | Windsor | 128/145.8 |
| 3,474,549 | 10/1969 | Schnell | 37/61 |
| 3,535,801 | 10/1970 | Richter | 37/61 |
| 3,673,716 | 7/1972 | Trondle | 37/61 |
| 3,709,214 | 1/1973 | Robertson | 128/6 X |

FOREIGN PATENTS OR APPLICATIONS

| 1,483,314 | 4/1967 | France | 128/6 |
|---|---|---|---|

Primary Examiner—Aldrich F. Medbery
Attorney, Agent, or Firm—James C. Wray

[57] ABSTRACT

High pressure oxygen is released through a side of an open-ended ventilating bronchoscope or laryngoscope into its lumen in a direction toward a distal end. The oxygen draws air through the proximal end. Medical gasses and vapors are drawn through an entrainment arm at the side of a ventilating endoscope by oxygen which is released near the distal point of confluence of the entrainment arm and the scope lumen.

10 Claims, 5 Drawing Figures

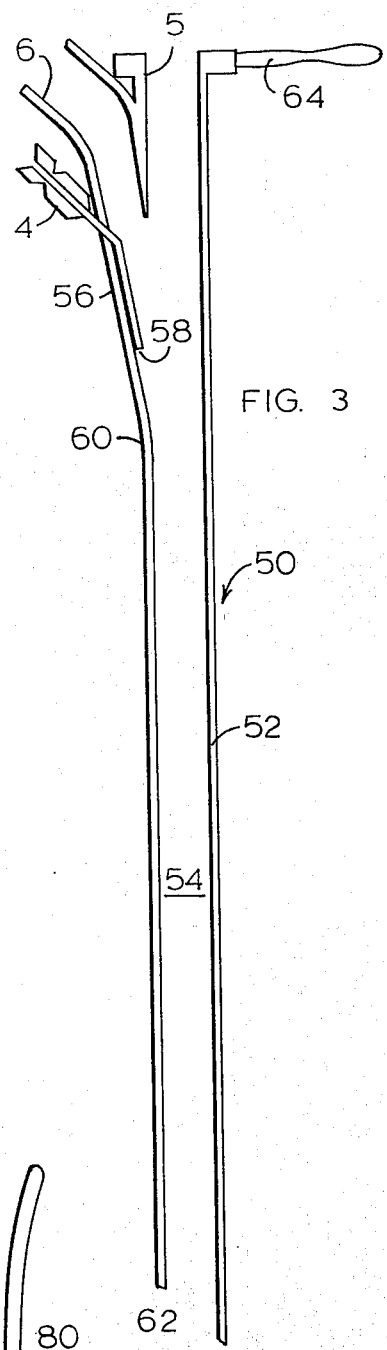
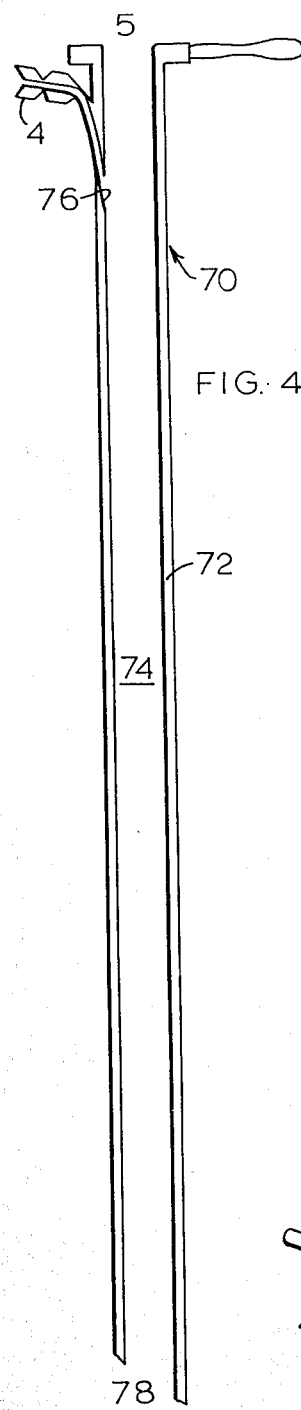
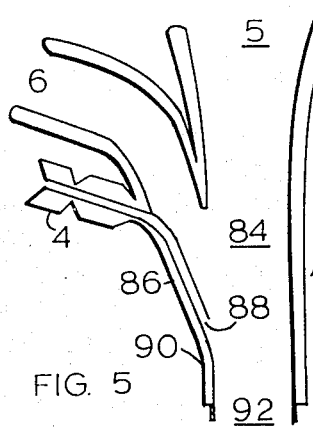

VENTILATING ENDOSCOPES

This is a continuation of application Ser. No. 249,665, filed May 2, 1972, and now abandoned.

An ideal situation for laryngoscopy or bronchoscopy under general anesthesia is to use the same laryngoscope or bronchoscope as a ventilating device which should provide an unobstructed view as well as means for instrumentation without hindrance.

One of the main problems during laryngoscopy and bronchoscopy under general anesthesia has been the competition between the anesthetist and the endoscopist, that is the laryngoscopist and the bronchoscopist, for the same anatomical area — the larynx and the tracheobronchial tree — as a situs for examination and surgery, and as an airway for augmented ventilation. One solution under such circumstances is to use the endoscope as a ventilating device and as means for delivering inhalation anesthetics. While the endoscopist uses the endoscope, that is the laryngoscopist uses the laryngoscope, or the bronchoscopist uses the bronchoscope, for brief or prolonged procedure, the anesthetist uses the same endoscope to ventilate the lung and to deliver anesthetics if desired. They would not interfere with each other's work. This technique should provide an unobstructed access and view of the desired anatomical area for instrumentation without hindrance. Augmented ventilation during laryngoscopic procedures can be accomplished with endotracheal tubes or cuirass respirators. However, this usually interferes with the procedure or obstructs a free and complete view of the larynx or is simply cumbersome and inefficient.

Several versions of ventilating bronchoscopes use the bronchoscope as an endotracheal tube. Ventilation and inhalation anesthesia are accomplished through a side arm and by means of glass or other covers to intermittently occlude the proximal end of the bronchoscope. This often obstructs the viewing and prevents instrumentation during bronchoscopy. It is now known to control ventilation during bronchoscopy by connecting an injector at the proximal end of a lumen of a bronchoscope. Intravenous anesthesia with muscle relaxant is usually used in such procedures. The injector is adaptable to different forms of bronchoscopes. However, it protrudes into the lumen of the bronchoscope. That obstructs viewing and hinders instrumentation during bronchoscopy. There is a lack of means for delivering inhalation anesthetics which are often desired or necessary.

SUMMARY OF THE INVENTION

Two versions of ventilating bronchoscopes and laryngoscopes using principles in fluid amplification are described, which provide means for augmented ventilation as well as means for delivering inhalation anesthetics during bronchoscopy and laryngoscopy, with scope and instrumentation without hindrance. For inhalation anesthesia and for other special purposes requiring medical gasses or vapors, an entrainment arm with reservoir bag is incorporated in one type of ventilating bronchoscope or laryngoscope for delivering predetermined gases or vapors. There is minimal attachment to the bronchoscope or laryngoscope — only a driving gas line in a simpler type of ventilating lumenscope. Intravenous anesthesia as well as inhalation anesthesia can be employed. Bronchoscopic and laryngoscopic procedures have been carried out with these endoscopes. Clinical experience and laboratory data provide evidence of adequate ventilation and satisfactory anesthesia during the procedures. The present invention has particular value in routine bronchoscopic and laryngoscopic procedures as well as in delicate or prolonged endoscopic procedures, among others, larynogoscopy and bronchoscopy in pediatric patients, selective bronchoscopy and laryngoscopy, and bronchography.

Two versions of a ventilating bronchoscope provide means for augmented ventilation and means for delivering inhalation anesthetics by using the principle of fluid amplification and by incorporation of the entrainment effect into the open lumen of the bronchoscope.

A preferred embodiment of a bronchoscope is constructed for augmented ventilation and for delivering inhalation anesthetics. The scope has a driving gas inlet in a specially designed entraining gas inlet — the entrainment arm — which runs into a medial portion of the bronchoscope near the proximal end and which has the same internal diameter as the bronchoscope. This entrainment arm provides means for delivering predetermined gas or vapor which might be inhalation anesthetics, oxygen, etc. Thus, controlled ventilation can be carried out during intravenous and/or inhalation anesthesia. The entrainment arm is positioned in the smallest angle possible with the axis of the main lumen of the bronchoscope. The driving gas inlet is parallel to the lumen of the entrainment arm and is located at its most distal end closest to but not into the lumen of the bronchoscope.

During the anesthesia process a reservoir bag is employed for the measured and vapors. A one-way valve may be inserted between the reservoir bag and the entrainment arm to prevent rebreathing. The reservoir bag deflates passively during inspiration and gas entrainment, and it refills during expiration.

During bronchoscopy with the present ventilating bronchoscopes, the controlled ventilation is accomplished with a conventional respirator such as a Bird Mark II Respirator or with Model 2 × 492 Speedair blowgun of the Inhalation Supply Co. of San Francisco, with a Regulator RO4-200-RGEA of the C. A. Norgren Co., or with any other device to interrupt the driving gas intermittently, such as a blowgun type device with a pressure regulator. The amplified gas mixture with its force and the resulting pressure are used to ventilate the lung.

A simpler form of bronchoscope is used solely for augmented ventilation during bronchoscopy with pressurized oxygen as the driving gas which entrains air. Intravenous anesthesia is used. The present ventilating bronchoscope differs from others in the location of the driving gas inlet. While another injector is inserted into the lumen of the bronchoscope, occupying some of the precious limited space during bronchoscopy, the present simpler type ventilating bronchoscope uses a metal needle soldered into the wall and a hole through the wall, near the proximal end of the bronchoscope as the driving gas inlet. The bronchoscope lumen is clear and free from obstruction. The driving gas inlet is built with the smallest angle possible preferably less than 10° with an axis of the main lumen of the scope, which is both the entrainment duct and the diffuser. The inlet and the scope are almost parallel to each other, thus creating a maximal possible entrainment by a device which does not interfere with vision or instrumentation. There is no other extra attachment except the driving gas line.

The application of the Bernoulli's principle and the Venturi effect in fluid amplification and consequently in the construction of injectors and entrainment ducts is well known. The entrainment is the result not only of the subatmospheric pressure, hence suction effect, created by the driving gas in the region of constriction, but also of its propulsive effect on the resting gas surrounding the jet. The entrainment is greatest when the driving gas inlet is centered in axial alignment with its diffuser; the driving gas may entrain as much as twenty times its own volume.

With the ventilating bronchoscope of the present invention, the injector nozzle is on the perimeter of the diffuser, in the wall of the bronchoscope. Thus, the entrainment is considerably less than that of the suitably designed injector and diffuser in an ideal entrainment duct. However, the amplified flow of gas and its resulting pressure is more than adequate for clinical purposes. The ventilation under such conditions has been excellent.

Flow measurements have been carried out with calibrated Fleisch Pneumotachographs mounted at the distal end of both types of ventilating bronchoscopes and at the proximal ends of the entrainment arms in the preferred scope, using pressurized oxygen in flow at various pressures as the driving gas. Pressure measurements have been carried out with Statham P23 transducers mounted at the distal ends of the bronchoscopes. The measurements have been recorded with a Grass Model 7 Polygraph. The preferred type ventilating bronchoscope can be made so that approximately fifty per cent of the total gas volume flow at the distal end of the bronchoscope is entrained from the entrainment arm, while the remaining 50 per cent consists of the driving gas and the entrained air from the proximal inlet of the scope. Thus, the concentration of the entrained agents from the entrainment arm is halved at the distal end of the bronchoscope and eventually goes into the lungs.

Many problems during laryngoscopy are common to those during bronchoscopy. Therefore, the same principles of fluid amplification have been extended to laryngoscopy. Two corresponding versions of ventilating laryngoscopes providing means for controlled ventilation as well as means for delivering inhalation anesthetics during laryngoscopy have been constructed and have been used clinically. The ventilation under such conditions has been excellent even with an open and unsealed connection between the laryngoscope and the larynx.

The universal or preferred form of ventilating bronchoscope is constructed for using inhalation anesthetics. The driving gas inlet is in a specially designed entraining gas inlet — the entraining arm — which runs into the wall of the scope near the proximal end of the laryngoscope. The entraining arm provides a means for delivering predetermined gas or vapor which might be inhalation anesthetics, anesthetic vapors, oxygen, etc. Thus, intravenous anesthesia and/or inhalation anesthesia can be produced. Controlled ventilation can be carried out. The special entraining arm with the driving gas inlet is parallel to the lumen of the special entrainment arm and is located at its most distal point closest to but not in the lumen of the laryngoscope.

During the anesthesia process a reservoir bag is used for the measured gases and vapors, and a one-way valve is used between the reservoir bag and the special entrainment arm to prevent rebreathing. The reservoir bag deflates automatically and passively during inspiration and gas entrainment and refills during expiration.

These ventilating laryngoscopes permit prolonged or brief delicate procedures under general anesthesia and controlled ventilation with a respirator, or a blowgun type device with a pressure regulator, or any other device to interrupt the driving gas — oxygen, intermittently. Adequate ventilation can be provided in intravenous as well as in inhalation anesthesia with muscle relaxation. There is minimal attachment to hinder the laryngoscopist using the ventilating laryngoscope. There is no endotracheal tube to obstruct the view of the entire larynx or to hinder the instrumentation. The lumen of the laryngoscope and the entire larynx is free of obstruction during the laryngoscopic procedure. The ventilation under such conditions has been excellent even with an open and unsealed connection between ventilating laryngoscope and larynx.

A simpler form is for ventilation during laryngoscopy with pressurized oxygen as the driving gas which entrains air. Intravenous anesthesia is used. A metal needle is soldered to a wall near the proximal end of the laryngoscope as an injector or driving gas inlet. This driving gas inlet is built with the smallest angle possible, preferably less than 10° with an axis of the main lumen of the scope, which is the entrainment duct and the diffuser. The axis of the main lumen and the inlet opening are almost parallel to each other, thus creating a maximal possible entrainment. The injection device does not interfere with vision or instrumentation in the scope. There is no other extra attachment except the driving gas line. The amplified gas mixture with its force is used to ventilate the patient.

Flow measurements have been carried out in the laboratory with Wright's Ventilometers mounted at the distal end of both types of ventilating laryngoscopes and at the proximal end of the entrainment arm in the preferred type scope, using continuous oxygen inflow at 20, 30 and 40 psi as the driving gas. Both types of ventilating laryngoscopes desribed produce similar degrees of amplification. The driving gas flow is amplified approximately 7 to 6 times at 20 to 40 psi. With the preferred type ventilating laryngoscope it has been found at each instance that approximately 50 per cent of the total gas volume flow at the distal end of the laryngoscope is entrained from the special entrainment arm, which the driving gas and the entrained air from the proximal inlet of the scope make up the remaining 50 per cent. The concentration of the entrained gas, vapor, etc., from the entrainment arm, e.g. inhalation anesthetics, are halved at the distal end of the laryngoscope.

General anesthesia for laryngoscopic procedure is often required. An unobstructed view of the entire larynx is certainly desired. A completely anesthetized and even paralyzed patient is especially important in many delicate laryngoscopic procedures, for instance microlaryngoscopic procedures and/or endolaryngeal procedures or microsurgery. This has been accomplished with general anesthesia and muscle relaxation. Ventilation is augmented through an endotracheal tube, which has been cumbersome and has become one of the two major obstacles during delicate laryngeal procedures.

The entrainment is greatest when the driving gas injector is centered in axial alignment with the diffuser. With a suitably designed injector and diffuser, the driving gas may entrain as much as 20 times its own volume. With the ventilating laryngoscope the injector nozzle is on the perimeter of the diffuser, in the wall of the laryngoscope. Thus, the entrainment is considerably less than that of a suitably designed injector and diffuser in an ideal entrainment duct. However, it is more than adequate for clinical purposes.

Although the simple form of ventilating laryngoscope has been proven very satisfactory with intravenous anesthesia in most of the adult patients, inhalation anesthesia and means of providing higher concentration of oxygen are often required or necessary in other isutations Therefor, the universal ventilating laryngoscope with the entrainment arm provides means for augmented ventilation as well as for delivering inhalation anesthetics and other gases. The clinical use of the ventilating laryngoscopes has proven successful in routine laryngoscopic examination, mocrolaryngeal surgery and laryngoscopic procedure where a paralyzed patient or prolonged time is desired. Blood gases testing provides evidence of adequate ventilation during various laryngoscopic procedures.

The two versions of ventilating laryngoscopes using principles of fluid amplification provide means of augmented ventilation during laryngoscopic procedures under general anesthesia and muscle relaxation with unobstructed views of the entire larynx. There is only minimal attachment to the laryngoscopes. Only a driving gas line is connected to the simpler ventilating laryngoscope. For special purposes a side arm with reservoir bag is incorporated in the universal type ventilating laryngoscope. Intravenous anesthesia as well as inhalation anesthesia can be used for laryngoscopy. Clinical experiences provide evidence of adequate ventilation and satisfactory anesthesia during various laryngoscopic procedures.

The broad objectives of this invention are accomplished by providing an open ended endoscope with a side wall inlet opening into the lumen of the scope in the direction of the distal end of the scope at a small acute angle to an axis of the lumen. A source of fluid under pressure, for example oxygen at from 10 to 80 psi, is connected to the inlet means. Releasing the fluid into the lumen of the scope toward the distal end draws ambient fluid, for example air, through the open proximal end of the scope, and the pressurized fluid and ambient fluid pass through the distal end of the scope, usually into the lungs. A fluid controller is connected to the pressure supply so that the movement of pressurized fluid and ambient fluid through the lumen toward the distal end of the scope may be controlled. Often the control is intermittent so that flow will be toward the distal end while pressure is supplied and so that flow may return from the distal end toward the proximal end when pressure is cut off.

In the preferred or universal embodiment of the invention, the inlet means includes a large entrainment duct which is connected to the side wall of the scope and which opens into the lumen, usually in the direction of the proximal end at an acute angle to an axis of the lumen. Pressurized fluid, usually oxygen, is released near the juncture or confluence of the entrainment duct and the scope. The released fluid draws fluid through the entrainment duct into the lumen toward the distal end of the scope as well as into the lumen through the proximal end of the scope toward the distal end. The universal type scope with the entrainment duct may be used when it is desired to supply a greater amount of ambient fluid in relation to the pressurized fluid, simply by leaving the entrainment duct open at its end remote from the scope. Often the entrainment duct is connected to a source of medical gasses or vapors such as, for example, anesthetics. In one embodiment, the anesthetics may be stored in a collapsible chamber at atmospheric pressure. The supply of pressurized fluid to the scope draws fluid from the container, collapsing the container, providing a measured dosage of fluid from the container into the lumen of the scope and through its distal end.

One object of the invention is the provision of ventilating endoscopes having high pressure inlet lines opening into lumens of the scopes at small acute angles in the direction of distal ends of the scopes.

Another object of the invention is the provision of ventilating endoscopes having entrainment ducts joined to the scopes at sides thereof near the proximal ends and having pressurized fluid inlets near the downstream point of the confluence for directing pressurized fluid into the lumen toward the distal end at a small acute angle with respect to an axis of the lumen.

Another object is accomplished by providing bronchoscopes constructed according to the present invention.

Another object is the provision of laryngoscopes constructed according to the present invention.

These and other objects of the invention are apparent in the disclosure, which includes the foregoing and ongoing specification and the claims and the drawings.

BRIEF DESCRIPTION OF THE DRAWINGS

FIG. 3 is a representation of a bronchoscope having an entrainment duct.

FIG. 4 is a representation of a bronchoscope for use in bronchoscopy under intravenous anesthesia.

FIG. 5 is a detail of ventilating endoscope apparatus with a distal end configured for connection to one of several attachment endoscopes.

DETAILED DESCRIPTION OF THE DRAWINGS

Throughout the drawings where possible, like numbers represent similar elements.

Figure 2:
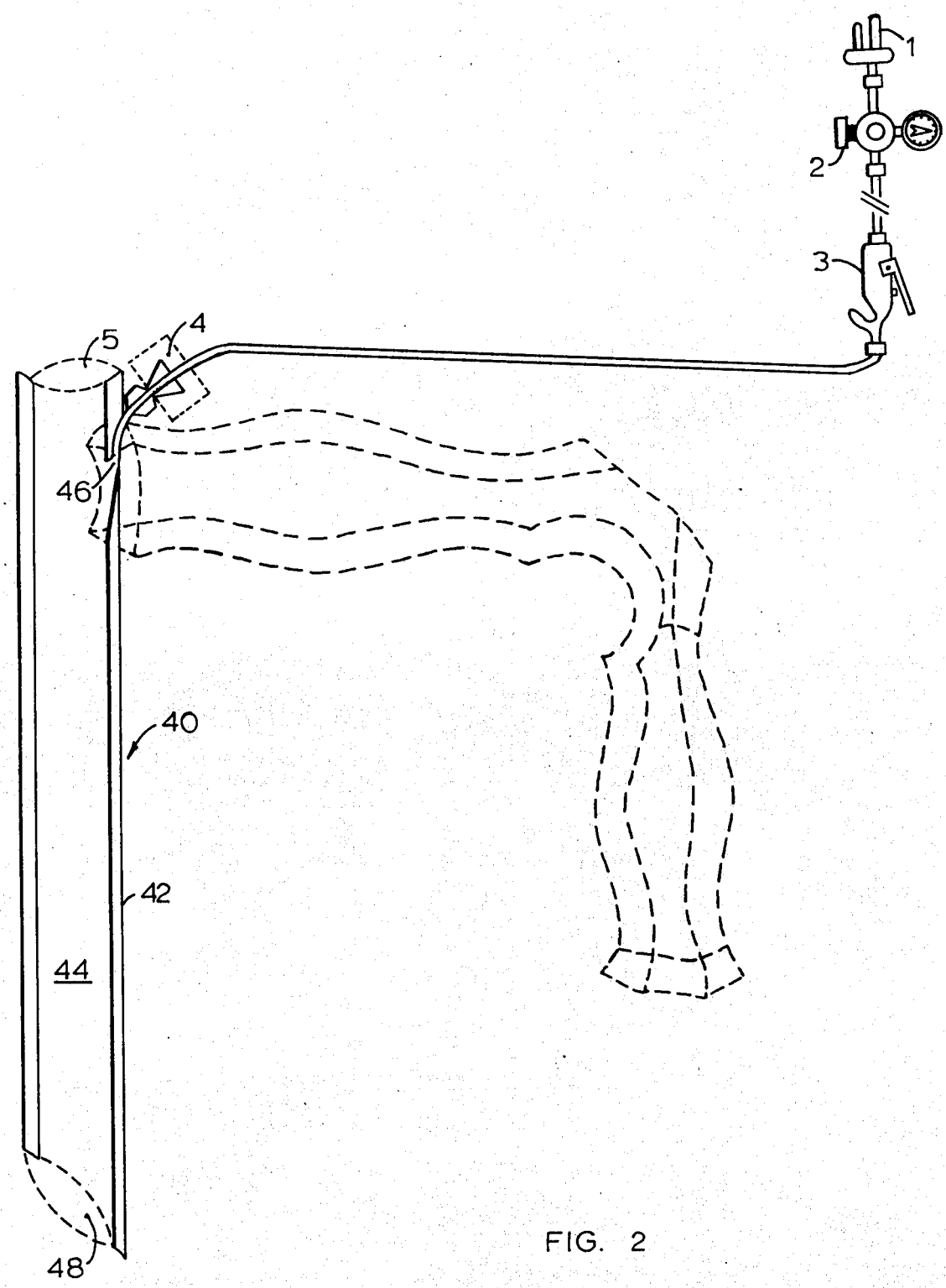
FIG. 2 is a schematic representation of a laryngoscope for use in ventilating during laryngoscopy under intravenous anesthesia.

Oxygen at 60 psi is supplied at input connection 1. An adjustable pressure regulator 2 contains the oxygen supply at the desired pressure. Interrupting apparatus 3 provides intermittent flow of the oxygen toward the inlet 4, which is connected to the endoscope so that air is drawn through the scope from the proximal end 5 toward the distal end. In modifications such as shown in FIGS. 2, 4 and 5, the inlet means comprises the high pressure oxygen inlet 4 which is connected in the entrainment duct 6.

Figure 1:
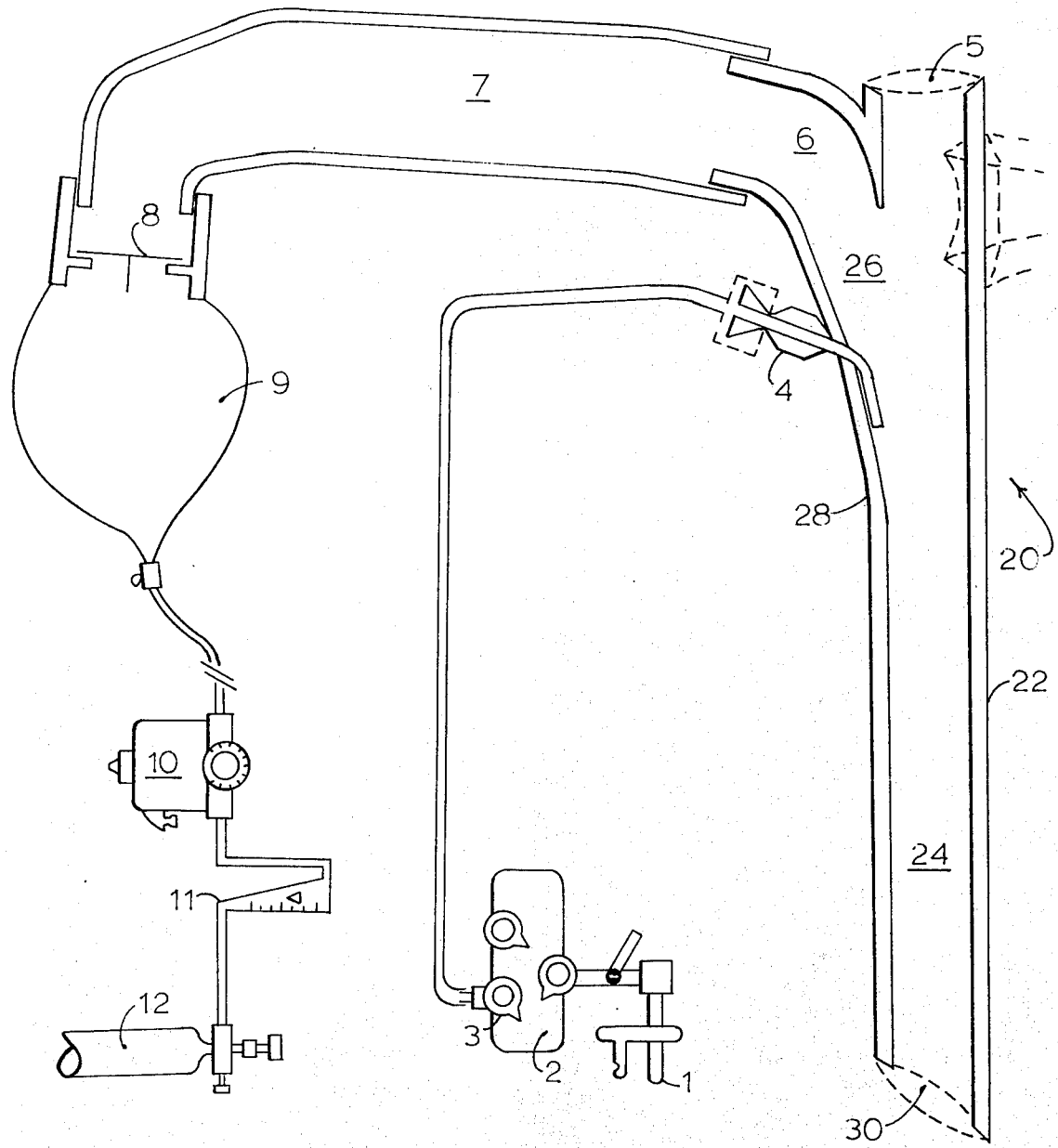
FIG. 1 is a schematic representation of a laryngoscope of the universal or preferred type of the present invention having a side entrainment arm and schematically showing the supplies connected thereto.

Referring to FIG. 1, a tube 7 connects the entrainment duct 6 with a one-way valve 8 on the outlet of collapsible container 9. As pressure is supplied through inlet 4, fluid is drawn from container 9 through the one-way valve 8 and entrainment duct 6 into the scope. Anesthetic vapors are supplied to the collapsible reservoir bag 9 from vaporizer 10 which is in turn supplied with oxygen from flow meter 11 and oxygen tank 12.

As shown in FIG. 1, a universal or preferred type of laryngoscope is generally indicated by the numeral 20. Scope 20 comprises a cylindrical wall 22, which defines a lumen 24. Wall 22 has an opening 26 to which is connected the inlet means, which comprises entrainment arm 6 and high pressure inlet 4. As shown in the drawing, inlet 4 opens near a distal point 28 of the juncture or confluence of entrainment arm 6 and lumen 24. For releasing pressurized gas into the lumen in a direction of the distal end 30 of scope 20 at a small acute angle with an axis of the lumen the angle may be 10° or less. In that manner, ambient fluid which is air is entrained through proximal end 5 and fluid is entrained from entrainment duct 6 into the scope and out through distal end 30.

As shown in FIG. 1, a respirator 32 has pressure regulating control 2 and intermittent feed control 3.

A laryngoscope generally indicated by the numeral 40 is shown in FIG. 2. A cylindrical wall 42 surrounds lumen 44. Pressurized gas inlet 4 is connected to wall 42 near proximal end 5 of the scope. The pressure inlet 4 releases oxygen into lumen 44 through hole 46 in wall 42. Hole 46 opens into lumen 44 at a very small angle with the axis of the lumen in a direction of distal end 48. The angle may be 10° or less, preferably less. Oxygen pressure is intermittently supplied by hand-controlled blowgun 3 from pressure regulator 2. A handle which is not part of the invention is shown in dashed lines.

A bronchoscope is generally referred to by the numeral 50 in FIG. 3. A cylindrical wall 52 encloses a lumen 54 in the open-ended bronchoscope. An inlet means generally indicated by the numeral 56 is connected to an opening in wall 52 near proximal end 5 of bronchoscope 50. The oulet end 58 of pressurized gas inlet 4 is mounted near a distal point 60 of an intersection of entrainment duct 5 and lumen 54. Pressurized gas is released from end 58 of inlet 4, entraining air through proximal end 5 and air or medical gasses and vapors through entrainment duct 6 and forcing the mixed air and vapors or gasses out of distal end 62.

A simple handle 64 is provided at the proximal end 5 of scope 50.

As shown in FIG. 4, bronchoscope 70 has a cylindrical wall 52 which surrounds lumen 74. Pressure inlet 4 extends into a hole 76 in wall 72 near proximal end 5. Preferably, the hole 76 forms an acute angle with an axis of lumen 74 at about 10° or less. Pressurized gas, usually oxygen, released through hole 76, entrains air through proximal end 5, thereby forcing air and gas through distal end 78.

In FIG. 5 a ventillating endoscope apparatus is generally indicated by the numeral 80. Wall 82 surrounds lumen 84. An inlet means is generally indicated by the numeral 86. End 88 of pressure inlet 4 opens near distal portion 90 of an inner section of entrainment duct 6 with lumen 84. Pressurized gas released from opening 88 entrains fluid from duct 6 and from open proximal end 5. Distal end 92 of endoscope 80 is configured for attachment to proximal ends of scopes of varied lengths, sizes or shapes.

Although the invention has been described with specific reference to preferred embodiments, modifications and variations may be made without departing from the invention. The scope of the invention is defined in the claims.

I claim:

1. Ventilating endoscope apparatus comprising an elongated endoscope having a length greater than a width, having a continuously open proximal end and a continuously open distal end, and an elongated wall means for laterally enclosing the scope between the open ends, thereby defining a lumen continuously open at opposite ends, fluid inlet means connected to and opening at a small angle along the wall means near the proximal end and fluid pressure means connected to the inlet means and the inlet means opening into the lumen in a direction toward the distal end for passing fluid from the inlet means into the lumen toward the distal end and entraining air through the proximal end into the lumen.

2. The apparatus of claim 1 further comprising a source of fluid pressure connected to the inlet means for pushing fluid through the inlet means into the lumen toward the distal end.

3. The apparatus of claim 2 wherein source comprises an intermittent pressure source.

4. The apparatus of claim 1 wherein the inlet means comprises a relatively fine hole through the wall means opening into the lumen at an acute angle to an elongated axis of the endoscope.

5. The apparatus of claim 4 wherein the hole opens into the lumen at an angle less than ten degrees to the elongated axis.

6. The apparatus of claim 1 wherein the inlet means comprises entrainment means connected to the wall means and opening into the lumen.

7. The apparatus of claim 6 wherein the fluid pressure means opens in the entrainment means near a distal point of an intersection of the entrainment means and the lumen, wherein fluid is entrained into the lumen through the entrainment means and the proximal end of the endoscope.

8. The apparatus of claim 1 wherein the endoscope is a bronchoscope.

9. The apparatus of claim 1 wherein the endoscope is a laryngoscope.

10. The apparatus of claim 1 wherein the endoscope is a proximal attachment for an elongated scope body.

* * * * *